US005635618A

United States Patent [19]
Capellades et al.

[11] Patent Number: 5,635,618
[45] Date of Patent: Jun. 3, 1997

[54] PROMOTER ELEMENTS OF CHIMERIC GENES OF α-TUBULIN

[75] Inventors: Montserrat Capellades, Barcelone, Spain; Richard De Rose, Lyons, France; Lluis Montoliu, Heidelberg, Germany; Pedro Puigdomenech, Barcelone, Spain; Miguel A. Torres, Barcelone, Spain; Javier Uribe, Barcelone, Spain; Juan Rigau, Barcelone, Spain

[73] Assignee: Rhone-Poulenc Agrochimie, France

[21] Appl. No.: 336,778

[22] Filed: Nov. 9, 1994

[30] Foreign Application Priority Data

Nov. 10, 1993 [FR] France ................. 93 13684

[51] Int. Cl.⁶ ............... C12N 5/14; C12N 15/82; C12N 15/09; C12N 15/29; A01H 5/00
[52] U.S. Cl. .......... 536/24.1; 536/24.2; 536/23.6; 435/172.3; 435/320.1; 435/413; 435/414; 435/415; 435/418; 800/DIG. 9; 800/DIG. 26; 800/DIG. 27; 800/DIG. 43; 800/DIG. 52; 800/DIG. 55; 800/DIG. 56; 800/205
[58] Field of Search ................. 536/23.6, 24.1, 536/24.2; 435/240.4, 320.1, 172.3; 800/205, DIG. 9, 26, 27, 43, 52, 55, 56

[56] References Cited

U.S. PATENT DOCUMENTS 5,086,169  2/1992  Mascarenhas ............... 536/27

FOREIGN PATENT DOCUMENTS

11443/92  9/1992  Australia .
0507698  10/1992  European Pat. Off. .

OTHER PUBLICATIONS

Kim et al. Plant Molecular Biology 24: 105–117 1994 A 20 nucleotide upstream element is essential.

L. Rigau, et al. (1993) "Analysis of a Maize Alpha–Tubulin Gene Promoter by Transient Expression and in Transgenic Tobacco Plants" *The Plant Journal* 4:6 1043–1060.

L. Montoliu, et al. (1989) "A Tandem of Alpha–Tubulin Genes Preferentially Expressed in Radicular Tissues from Zia Mays" *Plant Molecular Biology* 14 1–15.

J.L. Carpenter, et al. (1992) "Preferential Expression of an Alpha–Tubulin Gene of Arabidopsis in Pollen" *The Plant Cell* 4:5 557–571.

L. Montoliu, et al. (1990) "The Tubalpha3 Gene From Zea Mays: Structure and Expression in Dividing Plant Tissues" *Gene* 94 201–207.

J.L. Carpenter et al. (1993) "Semi–Constitutive Expression of an Arabidipsis Thaliana Alpha–Tubulin Gene" *Plant Molecular Biology* 21 937–942.

*Primary Examiner*—David T. Fox
*Assistant Examiner*—Thomas Haas
*Attorney, Agent, or Firm*—Scully, Scott Murphy and Presser

[57] ABSTRACT

Regulatory regions from maize α-tubulin genes are disclosed. In particular, 5' regulatory regions comprising an upstream regulatory ensemble (URE) from maize α-tubulin 1 and 3 genes is useful in tissue specific expression of heterologous genes in transformed plants. The maize α-tubulin URE comprises regulatory elements which when operably linked to a promoter and heterologous gene, confer regulated expression in roots, pollen and meristematic tissues. Expression constructs which confer tissue specific expression are also provided.

35 Claims, 3 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1529 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTCGAGAAGG  ACTACGAGGA  GGTTGGTGCT  GAGTTTGATG  AGGGTGAGGA  AGGTGATGAT      6 0

GGTGATGAGT  ACTAGAAGTA  TCCTGATGCG  GTCATCGTCA  GGCTTGTGTG  CTGCTCTTGT    1 2 0
```

-continued

| | | | | | | |
|---|---|---|---|---|---|---|
| CCCCGTTGTG | GTTTGCAACA | CCTGATGTTG | TAAGACTTTC | TGGTTATGTC | CGCCCCGCTG | 180 |
| TGCCACTGGG | TTATTAAGAA | CGTCGTTATG | GATGGTTGTC | TACACTACAT | TATTGCTTCT | 240 |
| CGATATTGGA | AAACTGTTAT | GCGCCTCGGT | GGATTGTGTT | GTTGTCGTAA | TGTCATCACT | 300 |
| CATACGCCGC | TGGGAATTTT | GAGGCCTGTC | AAGCATCAGG | ATTGCGTTAT | GAGTTAAATG | 360 |
| CTTCAGCGAC | GTTTAAACTT | GTCTAAGGTG | CCATCTAGAT | CATGAACTTG | TCAAGGGTTG | 420 |
| CCACTTAGAT | CATGAACTTC | GTAAATATGT | TTTTGGATCC | AAAATATGTT | TTTTATCCTT | 480 |
| AAGGGTGTGT | TTGTGTGTTT | GGTTGAATGT | ATAAGAAGGG | ATGAAGAGG | AATGTCATAA | 540 |
| TTTCTATAGT | GTTTGGTTGA | GAGACAAGTG | AGGACGAGAT | AAATACCTAA | GAAGGGATGA | 600 |
| AAGAGGAATG | CCACAATTTC | TATAGTGTTT | GGTTCAGAGA | CAAGTGACAA | TTTCTATAGT | 660 |
| GTTTGGTTGA | GAGACAAGTG | AGGGCGAGTA | ATACCGCAA | TAATTTTTG | GTGGCACCAA | 720 |
| ATTTTTGTGA | AGTTGTATAC | ATTTTGGACA | CCAATAGAAA | ATAGAATTAA | AAAAATATAA | 780 |
| AACTGGTGTC | ATTTAAATCA | GTGTCACGTT | ATTAAAATTT | AAAACTATCA | ACTAAAATTG | 840 |
| TCTAATGGAT | TATTTATGTG | GTTTTGTAAA | GTTGTGGAGA | TTAAACAACC | AGTTTTGAAG | 900 |
| ATAAGTAAGT | GAAATAGTCA | AATAGACCGT | ACTAAAGGTT | AAGAATTTAG | GTACACTTAC | 960 |
| GACTAGTTTA | GATGCCGCAA | AATGGGTTAA | ATTTTCTTC | TTATTCAAAA | TTAAATAATA | 1020 |
| AGGTGAATTT | AACTACTCTA | ATTTCCTCTG | TTTTTTAAC | TCCCAAACTA | TCCCTTATTC | 1080 |
| GTAATAATAG | GAAGCGGTGA | CAGTTGGTG | GTGAGAACTC | AGGTATCAAC | AAAAAGAAAT | 1140 |
| GTATTTTGA | AATATTTGC | TCGTAATGCC | CTGCAAGGTT | TCGATTTCCG | TAGCCAGTAC | 1200 |
| ATGTCCGCTC | TTGACCCAGG | TACTGTGACA | CGAACCAACC | GACCGTTGAA | CGGACGTGGA | 1260 |
| GCACGAACCA | TTAAAACAAT | CAAAATCTCA | GGGGCTCAAA | CGAAAAAACA | CCGCCCCCTT | 1320 |
| CCCTCGCTTG | CGCTGGCACT | CCATCGTGGG | CTCGTGGCCC | AGGCTGTCGT | TCTGTTCTAT | 1380 |
| AAAGCGAGAC | GAGTGGGAGC | AGGCGTAACC | CTAATTGAGC | ATCGCAGAGA | TAGGCGTCTT | 1440 |
| CGTACTCGCC | TACCTCCGCG | GCTCAAACCT | TTCCCCCTTC | TCCCAATTCC | TTCCGCCGGC | 1500 |
| CGCCGCTCCA | CCCGTACGAC | GACACCATG | | | | 1529 |

( 2 ) INFORMATION FOR SEQ ID NO:2:

( i ) SEQUENCE CHARACTERISTICS:
        ( A ) LENGTH: 1765 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| GAATTCCCTT | TGTGAGAAAT | CTCCACAAGT | TGGAGCCTCT | CACCCTTACA | AGATTGATCA | 60 |
| CAATTAAACC | ACAAGAGTAA | GGGAGGGAAC | AGAAACACAC | ACAAGTGCTA | GAGTCGCAGC | 120 |
| AATGACATGC | ACACAAGTCA | AGAAACGAGC | ACACAACACA | GCGCAACGAG | CTCACAGTTC | 180 |
| AAACAAGTGC | TCAAATCTTA | AACACAATGA | ATCGAATGCG | TGCTTGCGGA | GTCTAGACGT | 240 |
| TTTTTCAATG | GAGGCTTGGT | GTACTGCTCC | ATGTGTCTAG | GGGTCCCTTT | TATAGCCCCA | 300 |
| AGGCAGCTAG | GAGCCGTTGG | AGCTCCATTT | GGAAGGCCAT | TGTTGCCTTC | TATCCGTGGG | 360 |
| TGCACCGGAC | AGTACGCGCT | CGGGACGCGG | CACATAATCC | CATGATTGGC | CGGTTTCCGC | 420 |
| TTCTGGGGGC | ACCAGACGGT | CCAGACGACC | AGTGCGCCTG | TCGACCGTTG | GCCAGCGCTG | 480 |
| ACGTGGCCAC | TAGTCGTTGC | GTGGCTGATA | CAACAGACTG | TTCGGCGCAT | TGCGGACCAT | 540 |
| CCGGTGAATT | ATAGCTGATG | TAGGCTAAAA | AACCCGAGAG | CAGCGAGTTC | GGCCGAACCG | 600 |

| | | | | | | |
|---|---|---|---|---|---|---|
| TGCACCAGAC | TGTATGGTGG | GTGGCATCAG | ACCGTTCGGT | GCTACACAGT | CTAGCAACTT | 660 |
| TTCCCTGTTT | CTTCTTTTGT | CTTCTTTGTT | TCTTTTGGAC | TTCACTTAGC | TGGGTCCCCT | 720 |
| GGCACTTAGA | CAAATATGAT | TAACACTCAA | ATCAATTGAC | TTAGTGTCTA | GAGCATACCT | 780 |
| TTTAGCTTGA | TCCATATAGC | TTTGTACTAA | GTCCTCTTCC | GAGCTCATTT | TGCCTCACAC | 840 |
| TTTTGCTTAA | CATCATGTTA | GTTCAAACAT | CATGTGTTGT | GCATCTAATC | ACCAAACCAA | 900 |
| TATAGAAATG | CCCAAGGACA | CATTTCCCTT | TCAGTCGGGG | GGAGGGGGT | TGGTGGTCGA | 960 |
| CGCCCCGGTA | CGAAGTGGGT | GGGGGCAGGC | GAGAGGGGGT | GCACCATGGG | CCACCCAGTG | 1020 |
| CGTGGTCCGG | TTTTGATCCA | TGTAACTCTA | TATAAATCTC | TATTTAATTC | GGTATAAAAT | 1080 |
| AGTTAAGATG | AAAGAGAGAA | TAAAATTTAG | TAGATTTGAC | AGTCATATAA | AATTTCTAGA | 1140 |
| TCGACCCCTG | TGGTGGGTGC | GTCGAAATTT | CTAGACCGCC | CTAGGCGGG | GATGACACAT | 1200 |
| GGAACCGTGT | ATGCACAAAG | CTGCTGCATT | ATAATTGTAG | AGATTAATTA | TGTTATTTAG | 1260 |
| GAAATAAAAG | TTTAGGAATA | GTATATAAAA | CAAGGATTGA | GCTCCAGATA | TATAATAGGC | 1320 |
| CGAGTCCTGT | AATTTGTGA | CATTTTTTG | AAACCAGGAT | TGAGCTGCAG | TTTTAGTGT | 1380 |
| TAGAGTCCAG | CGTCTCACAG | GAGTGGTCCA | ATTCAAATTC | GAAAATGTAT | CACCGCTGAA | 1440 |
| GCGAAAAATA | TCATAAATTC | ATAACGAACC | AACCGACCGT | TGCACGGACG | AGAACTCGAC | 1500 |
| GAGACCGAAC | CGTGAAAACA | ACCGAAAGCA | CAGGGCTCA | AACGAAACAA | TCCCGCCCAC | 1560 |
| ACTTCCTTCG | CCGGCTCATG | GTGGCCACTG | GCCAGGCTGT | CATCCTGGTC | TATAAAGCGA | 1620 |
| GCCGAGGGGA | AGAGCCGGAA | CCCTAGCCCA | GCACCGCAGA | GGCGCAGAGA | CAGGCGTCTT | 1680 |
| CGTACTCGCC | TATCTCCGCG | ACTCAAAGCT | TCTTCCATTT | CCTACCGCCG | CCGCTGCAGC | 1740 |
| TCCACCCCAT | TCCGTCGACA | CCATG | | | | 1765 |

( 2 ) INFORMATION FOR SEQ ID NO:3:

( i ) SEQUENCE CHARACTERISTICS:
        ( A ) LENGTH: 1179 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| AGATCTTGAT | TCTGTGCAGT | GCTGGTGATG | GGAAAAAGCG | AAAACCATC | GGTATGTTTT | 60 |
| TGACAAATAT | GAAATGGGA | CAAAACAAC | ATGTGTGTTT | TTTCGACCGT | TTCCGCTTTT | 120 |
| CTTGTTTTAG | TCACAATAGC | TCGTTTTTAT | CCACATATGA | TATCTCATTT | TAGATAATAC | 180 |
| ATGAACAAAT | CATAATTGAT | TATATCATAT | CTCAACAAAT | TAACCCGTAA | TGAATTATTT | 240 |
| TTCTTTGATA | GTCATATGTA | CATTACAATA | TTTCGCTTCC | ATATGTATGG | ATGTGATGTT | 300 |
| TTAATCGATT | GCAACACTAC | TTTTATTTTT | ATACTCTATG | TGACAATTAT | TTCCGCTTTT | 360 |
| ATTTACATCT | TATTCCGATC | TGTTATCGAT | ATCGATTTGT | TCCGTCCCGT | TTTTATCTTA | 420 |
| TTTCTGATAG | TTCCAATTTA | ATCTTATTTT | CGAAATAAAG | TATGAAAATA | AAAATAAGAG | 480 |
| AGATTGTTAC | GTTCGATCCG | GTTTGAACC | CTAGCTATAC | TTGCCCGTTG | TTGCAACTGG | 540 |
| CCGGCCATTC | CATAGGCGGG | CACAGTCAGC | ACTCAGCAGT | GACAGAGTGC | GCGTGCGACA | 600 |
| CACAGTTTCA | AATTTCAAAA | CTGAACGGG | CGGCTATAAA | CAGAACCCGC | TGCTCCCAGG | 660 |
| AGCCTCACGC | AGATAAATTC | ACCCACATCA | ATGGGGCCCA | AATATTTATA | ACCATCTATT | 720 |
| GGTCCCACAT | GTTCGTGTCA | CAACATCCTC | TACCGCAGGT | AAAGATAGCC | GTCTCGCCAA | 780 |

| | | | | | | |
|---|---|---|---|---|---|---|
| GACCCCGAGC | CCGCCGCTGC | CCGGACCCGC | CGCCAGCTCA | CACCCACCGT | TGCCGGCCGC | 840 |
| TGAGCCGTTC | GAAGCCAAAA | CGGTCGTTAA | CCACCCAGCT | GCCCGTCGGC | TACCATCACG | 900 |
| CCGTTAGCCC | CGAACCAGAC | GGCGGCTAGG | TCTTCCGCCG | CGCGCCGCGC | CATCACGGGC | 960 |
| CGGCCGCGGC | CTTCTTTCCC | ACGCTGCCTA | TAAAAGCCGC | CGCGGGGCTG | AGCAGCATTA | 1020 |
| TCGCTTCAGC | TCGGCGTCTT | CACAAACGCC | GGCGCAAACT | CTCGCCCGAG | CCCGACAGAT | 1080 |
| CTTCAATTCC | CCATTCCGCC | CACCGATCGA | CCTTCACGCC | AGTCTCGGTC | TCTTCCGAAG | 1140 |
| GCGTCGCGCG | CGGTTGTTTG | AGAGGGAGG | AGGAAGATG | | | 1179 |

( 2 ) INFORMATION FOR SEQ ID NO:4:

( i ) SEQUENCE CHARACTERISTICS:
        ( A ) LENGTH: 405 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| GAATTCCGAA | AGACAAAGAT | TATCGCCATG | GCTTCGATCT | CCTCCTCAGT | CGCGACCGTT | 60 |
| AGCCGGACCG | CCCCTGCTCA | GGCCAACATG | GTGGCTCCGT | TCACCGGCCT | TAAGTCCAAC | 120 |
| GCCGCCTTCC | CCACCACCAA | GAAGGCTAAC | GACTTCTCCA | CCCTTCCCAG | CAACGGTGGT | 180 |
| GGAAGAGTTC | AATGTATGCA | GGTGTGGCCG | GCCTACGGCA | ACAAGAAGTT | CGAGACGCTG | 240 |
| TCGTACCTGC | CGCCGCTGTC | AATGGCGCCC | ACCGTGATGA | TGGCCTCGTC | GGCCACCGCC | 300 |
| GTCGCTCCGT | TCCAGGGGCT | CAAGTCCACC | GCCAGCCTCC | CCGTCGCCCG | CCGCTCCTCC | 360 |
| AGAAGCCTCG | GCAACGTCAG | CAACGGCGGA | AGGATCCGGT | GCATG | | 405 |

PROMOTER ELEMENTS OF CHIMERIC GENES OF α-TUBULIN

BACKGROUND OF THE INVENTION

The microtubules are essential elements for numerous functions in all sorts of cells. In plants in particular, they play a central role in several important phenomena, in particular those relating to morphogenesis. In all eukaryotes, the microtubules are composed of a large number of highly conserved proteins, the most abundant being the tubulins. Two principle subunits of proteins have been described, which are called α-tubulin and β-tubulin. The essential functions of the microtubules and their ubiquitous distribution have often suggested the idea that the genes encoding tubulins are a good example of highly and structurally expressed genes. In fact, the subunits of tubulin are encoded in eukaryotes by a family of genes. In the plant domain, the α- and β-tubulins have been studied in some plants such as maize, Arabidopsis, soya bean, peas and carrot. In all these cases, the respective genomes encode multiple α- and β-tubulin genes which are differently expressed during the development of the plant. In Arabidopsis, careful analysis of a family of tubulin genes revealed 15 genes (6 α-tubulins and 9 β-tubulins) encoding these proteins (Kopczak et al., 1992; Snustad et al., 1992). In maize, 3 α-tubulin genes have been cloned and sequenced (Montoliu et al., 1989; Montoliu et al., 1990), and six others can be detected by PCR analysis of the genomic DNA (Montoliu et al., 1992). According to a recent study, at least six DNA sequences of distinct α-tubulins were cloned and characterized from maize tissues (Villemur et al., 1992).

The α-Tub 1 and α-Tub 2 genes derived from maize are arranged in tandem, separated by at least 2 kilobase (kb) pairs of DNA. They are expressed in all maize meristematic tissues with high levels of expression in the radicular system (Montoliu et al., 1989). The α-Tub 1 gene is expressed in all the analyzed tissues at a higher level than the α-Tub 2 gene and is, in addition, highly expressed in the pollen (Montoliu et al., 1990). Hybridization experiments in vitro show that inside meristematic tissues, the α-Tub 1 gene is expressed during the quiescent central activation (Rigau et al. in Press). In Arabidopsis, a gene was found to be specifically expressed in pollen but none showed the same pattern of expression as the maize genes α-Tub 1 or α-Tub 2 (Carpenter et al., 1990). The maize gene α-Tub 3 is expressed in all plant organs which have a high content of cellulose undergoing division, in particular in the immature embryos (Montoliu et al., 1990).

It has now been found that the promoter regulatory elements of the regions derived from maize α-tubulin genes can control a specific tissue expression in the pollen, the radicular systems, the meristematic zones and the immature embryos of plant species, both monocotyledons and dicotyledons. The present invention permits greater control of gene expression in the transgenic plants, permitting especially better control of the herbicide resistance genes.

SUMMARY OF THE INVENTION

The subject of the present invention is the 5' regulatory region of a maize α-tubulin gene. This region is defined, in the present invention, as an upstream regulatory ensemble (URE), which is useful for controlling the expression of genes encoding heterologous genes. The URE comprises several regulatory elements, which create distinct patterns of regulated expression, when they are linked to the coding regions of heterologous genes expressed in transgenic plants. In particular, the present invention provides information relating to the regions isolated from the DNA derived from maize genes α-Tub 1, which controls specifically the expression of the genes in the roots, the pollen and the meristematic tissues.

Another aspect of the invention relates to plant chimeric genes containing these regulatory elements. The regulatory elements are functionally linked to the coding sequence of the heterologous gene, such that the regulatory element is capable of controlling the expression of the product encoded by the heterologous gene. If necessary, other promoter elements, either wholly or partially, are included in the chimeric gene constructs. These complementary elements comprise, but are not limited to, the intron sequences of monocots such as intron 1 of the rice actin gene, which greatly reinforces the expression of heterologous genes in the tissues of monocots. The invention also comprises plant transformation vectors as well as the plant cells transformed by these vectors and plants and the seeds containing the chimeric gene.

According to another aspect of the invention, chimeric genes are produced comprising a DNA sequence encoding a fusion polypeptide containing an amino-terminal transit peptide, which is capable of directing the subcellular localization of heterologous peptides towards the subcellular organelles specific for plant cells, with the obtaining of an increased control and a better targeting of the genetic expression in the transgenic plants.

The subject of the invention is also a process for producing transformed monocot or dicot plants, having a new property and which are especially resistant to herbicides. The plant cells transformed with this construct can give rise, by regeneration and/or culture, to resistant plants.

The present invention comprises cis regulatory elements of the upstream regulatory ensemble (URE) of maize α-tubulin genes. These cis regulatory elements are discrete regions of the URE, which confer regulation of the expression on the genes under their control. In particular, the invention comprises an isolated nucleic acid containing at least one gene element permitting specific expression in the roots, in the pollen, in the meristems and the immature embryos. Any tubulin gene can form the regulatory elements, especially, alone or in combination, the maize genes α-Tub 1, α-Tub 2 and α-Tub 3, which represent three similar α-tubulin genes. Preferably, the maize α-tubulin gene α-Tub 1 is used as source of regulatory elements.

One of the regulatory elements according to the invention comprises the specific gene expression in the roots. One regulatory element specific for the roots comprises a particular nucleotide sequence which is capable of initiating the expression of a gene under its control in the roots, that is to say for the product of the expression of the gene detected in the roots. The expression which is specific for the roots may be found in any part of the root, for example but with no limitation being implied, the meristematic zones of the roots, the lateral buds of the roots, the lateral roots and the vascular zones of the roots. No gene expression is detected in the tips of shoots, the stems or the leaves.

To identify the regulatory elements which control the gene expression specific for roots, analysis by deletion of the entire URE from a maize α-tubulin gene should be carried out. In a deletion analysis, the nucleotides of the entire URE are removed successively and the resulting fragments are ligated to the coding sequence of a reporter gene or to another heterologous encoding sequence. The constructs are then analyzed for their ability to control the gene expression specific for the tissues by detecting the presence of the heterologous gene product in the desired specific tissues excluding other tissues. The tissue-specific elements which were identified can also be modified, for example by site-directed mutagenesis. The modified regulatory elements can then be tested for their ability to control the specific gene expression in tissues and thus identifying the other sequences which confer the specificity in the tissues. These techniques for the identification of the regulatory elements are applicable to all the maize α-tubulin genes. For example, in a preferred manner, analysis of the URE of the maize α-tubulin gene α-Tub 1 indicates that the regulatory elements, which control the gene expression specific for the roots, consist of nucleotides 963 to 1115 and 1 to 1115 of the sequence represented ID No.: 1.

Other regulatory elements according to the invention control the gene expression specific for the pollen. The gene expression specific for the pollen is of particular interest and importance. Normally, the maize α-tubulin gene α-Tub 1 is expressed both in the roots and the pollen. When particular regions of the maize α-tubulin gene α-Tub 1 are isolated from the entire URE according to the invention, the expression is exclusively localized in the pollen. A regulatory element specific for the pollen comprises a particular nucleotide sequence which is capable of initiating the expression of a gene under its control in the pollen, that is to say for the product of the gene detected in the pollen excluding other tissues. The regulatory elements which control the expression specific for the pollen are identified by analyzing the fragments of maize α-tubulin gene for their ability to control the gene expression specific for the pollen, as described above for the identification of the regulatory elements specific for the roots except that the expression is detected in the pollen. The modifications of the nucleotide sequences permitting the expression specific for the pollen are identified as described above. The regulatory elements specific for the pollen, which are derived from any maize α-tubulin gene, can be identified by these techniques. For example, in a preferred mariner, analysis of the URE of the maize α-tubulin gene, α-Tub 1 indicates that the regulatory elements, which control the gene expression specific for the pollen, consist of nucleotides 1 to 1348 and 1295 to 1348 of the sequence represented SEQ ID No.: 1.

Other regulatory elements according to the invention, which are present in the URE regions of the maize α-tubulin gene, control the gene expression specific for the meristems. The regulatory elements which confer the gene expression specific for the meristems are identified as described above for the identification of the other regulatory elements. For example, deletion analysis can be used to identify the nucleotide sequences of any maize α-tubulin gene which controls the expression of a gene under its control in the meristems. Such sequences can be modified as described above and tested in order to identify other sequences which confer the gene expression specific for the meristems. For example, in a preferred manner, analysis of the URE of the maize α-tubulin gene α-Tub 3 indicates that the regulatory elements which control the gene expression specific for the pollen consist of nucleotides 1 to 695 and 542 to 695 of the sequence represented SEQ ID No.: 3.

Other regulatory elements according to the invention, which are present in the URE regions of the maize α-tubulin gene, control the gene expression specific for the immature embryos. The regulatory elements which confer the gene expression specific for the immature embryos are identified as described above for the identification of the other regulatory elements. For example, deletion analysis can be used to identify the nucleotide sequences of any maize α-tubulin gene which controls the expression of a gene under its control in the immature embryos. Such sequences can be modified as described above and tested in order to identify other sequences which confer the gene expression specific for the immature embryos. For example, in a preferred manner, analysis of the URE of the maize α-tubulin gene α-Tub 3 indicates that the regulatory elements which control the gene expression specific for the immature embryos consist of nucleotides 1 to 1076 of the sequence represented SEQ ID No.: 3.

It is possible to obtain an isolated nucleic acid encoding the upstream regulatory ensemble of a maize α-tubulin gene in the following manner. α-Tubulin recombinant genomic clones are isolated by screening a maize genomic DNA library with an α-tubulin cDNA (Montoliu et al., 1989). Useful methods for obtaining α-tubulin recombinant DNA are described in Ausubel et al., 1989, Current Protocols in Molecular Biology, John Wiley & Sons, N.Y., for example, or any one of the very numerous manuals on recombinant DNA technology, which are widely available. For the determination of nucleotide sequences, a multitude of techniques are available and known to the person skilled in the art. For example, the URE of the α-tubulin gene can be subcloned into a polylinker site of a sequencing vector such as pBluescript (Stratagene). These pBluescript subclones can then be sequenced by the "double strand dideoxy" method (Chen and Seeburg, 1985 *DNA* 4, 165).

The nucleotide sequence for the DNA encoding the α-Tub 1 clone of the URE of the maize α-tubulin gene is represented as SEQ ID No.: 1.

The nucleotide sequence for the DNA encoding the α-Tub 2 clone of the URE of the maize α-tubulin gene is represented as SEQ ID No.: 2.

The nucleotide sequence for the DNA encoding the α-Tub 3 clone of the URE of the maize α-tubulin gene is represented as SEQ ID No.: 3.

The nucleotide sequence for the optimized transit peptide is represented as SEQ ID No.: 4.

The UREs of other maize α-tubulin genes can be obtained using the same strategy. Moreover, clones representative of other members of the family of maize α-tubulin genes can be obtained using the transcribed sequences of the URE of α-Tub 1, α-Tub 2 and α-Tub 3 as hybridization probes in order to screen a maize genomic DNA library and to identify other α-tubulin genes.

The identification of cis regulatory sequences which control the specific gene expression in tissues can be carried out by transcriptional fusions of specific sequences with the coding sequence of a heterologous gene, transferring the chimeric gene into an appropriate host and detecting the expression of the heterologous gene. The test used for detecting the expression depends on the nature of the heterologous sequence. For example, reporter genes, such as that of β-glucuronidase (GUS), are commonly used to establish the transcriptional and translational competence of the chimeric construct. Standard tests are available for detecting sensitively the reporter enzyme in a transgenic organism. The GUS gene is useful as reporter for a promoter activity in the transgenic plants because of the high stability of the enzyme in plant cells and the availability of a quantitative fluorometric test and a histochemical localization technique. Jefferson et al., 1987 *EMBO J* 6, 3901, have given out standard procedures for the biochemical and histochemical detection of the GUS activity in plant tissues. The biochemical tests are carried out by mixing plant tissue lysates with 4-methylumbelliferyl-β-D-glucuranide, a fluorometric substrate for GUS, and then incubating for one hour at 37° C. and then measuring the fluorescence of the 4-methylumbelliferone. The histochemical localization of the GUS activity is determined by incubating samples of plant tissues in 5-bromo-4-chloro-3-indolyl-glucuronide (X-Gluc) for 18 hours at 37° C. and observing the pattern of X-Gluc spots. The construction of such chimeric genes permits a definition of the specific regulatory sequences necessary for regulating the expression and demonstrates by analysis that these sequences may control the expression of heterologous genes.

The present invention also comprises a plant chimeric gene containing a regulatory element derived from a maize α-tubulin gene, which controls the specific gene expression in the roots, the specific gene expression in the pollen, the specific gene expression in the meristem or the specific gene expression in the immature embryos and linked to the coding sequence of a heterologous gene such that the regulatory element is capable of controlling the heterologous gene. The heterologous gene can be any gene other than the maize α-tubulin gene. If necessary, it is possible to include in the chimeric constructs other promoter elements, either wholly or partially, such as introns of monocots sufficient for their expression to produce an effective quantity of polypeptide encoded by the heterologous gene and providing any useful agronomic property such as resistance to insects, to nematodes, to fungi and preferably to herbicides.

Consequently, the present invention comprises chimeric genes comprising regions of the URE of maize α-tubulin, which confers an expression specific for the roots according to the invention, which are linked to a sequence encoding a herbicide resistance enzyme. Preferably, the URE regions comprise nucleotides 1 to 1115, 963 to 1115 or 1 to 1529 of α-Tub 1, as indicated in SEQ ID No.: 1. Any modification of these conferring an expression specific for the roots forms part of the invention. The roots accumulate certain classes of herbicides, which make them very sensitive to applications of these herbicides in low doses. As the elements of the URE of the maize α-tubulin can control a high, regulated expression in the roots, they are useful for giving a resistance phenotype. These elements are useful for regulating the expression of genes encoding herbicide resistance enzymes such as the aroA from S. typhimurium and the enzymes for the detoxification of herbicides, such as the brx gene from K. ozaenae which is resistant to bromoxynil. Chimeric genes containing these elements can be used to produce transgenic plant lines resistant to agronomic doses of herbicides.

The invention also comprises chimeric genes having a region of the URE of maize α-tubulin which confers an expression specific for the pollen and fused with the heterologous gene. This construct confers an expression spatially distinct from the "normal" expression of maize α-tubulin in that the heterologous gene is expressed directly in the plant pollen. In other words, when a specific sequence is removed from the context of the URE, the specific regulation of the tissue is modified. Preferably, the URE regions of α-Tub 1 comprise nucleotides 1 to 1348 or 295 to 1348, as indicated in SEQ ID No.: 1. Also preferably, this regulatory element may be fused with cytotoxic proteins to create sterile male plants. Any modification of these conferring an expression specific for the pollen forms part of the invention.

The invention also comprises chimeric genes having a region of the URE of maize α-tubulin which confers an expression specific for the meristems and fused with a heterologous gene. Preferably, the URE regions of α-Tub 3 comprise nucleotides 1 to 695 or 542 to 695, as indicated in SEQ ID No.: 3. Any modification of these conferring an expression specific for the meristems forms part of the invention.

The invention also comprises chimeric genes having a region of the URE of maize α-tubulin which confers an expression specific for the immature embryos and fused with a heterologous gene. Preferably, the URE regions of α-Tub 3 comprise nucleotides 1 to 1076, as indicated in SEQ ID No.: 3. Any modification of these conferring an expression specific for the immature embryos forms part of the invention.

The use of these chimeric constructs is particularly important for providing herbicide resistance. As most herbicides do not distinguish between weeds and crops, genetic engineering of crop plants which are resistant to herbicides is of considerable agronomic importance since it allows the use of broad-spectrum herbicides. Consequently, the present invention comprises chimeric genes comprising elements of the URE of maize α-tubulin which confer an expression specific for the roots on at least part of a promoter, which functions in the plants and which, furthermore, is fused with at least part of the aroA gene or a sequence encoding a polypeptide conferring the herbicide resistance. As examples, there may be mentioned polypeptides conferring a resistance to glyphosate, and to the inihibitors close to 5-enolpyruvylshikimic acid-3-phosphate synthase (EPSPS), sulphonylureas, imidazolinones and inhibitors of acetoxyhydroxy acid synthase (AHS), and 4-hydroxyphenylpyruvate dioxygenase (HPPO). Preferably, the URE regions of α-Tub 1 comprise nucleotides 1 to 115, 963 to 1115 or 1 to 1529 as indicated in SEQ ID No.: 1 and are fused to the reporter gene. Any modification of these conferring an expression specific for the immature embryos forms part of the invention.

The chimeric genes according to the invention are constructed by fusing a promoter sequence, either partial or whole, of maize α-tubulin with the coding sequence of a heterologous gene. The juxtaposition of these sequences can be performed in many ways. Preferably, the order of the sequences, from 5' to 3' is as follows: URE of maize α-tubulin, a monocot or dicot, for example, tobacco, intron sequence, a coding sequence and a polyadenylation site.

The conventional methods for constructing such chimeric genes are well known to the person skilled in the art and can be found in references such as Ausubel et at. (1989). Various strategies are available for ligating the DNA fragments, the choice depending on the nature of the ends of the DNA fragments. A person skilled in the art knows that for the heterologous gene to be expressed, the construct requires promoter elements and signals for an efficient polyadenylation of the transcript. Consequently, the regions of the URE of maize α-tubulin which contain the promoter sequences known as CAAT and TATA boxes can be fused directly with a coding sequence without promoter. Moreover, the regions of the URE of maize α-tubulin which do not contain CAAT and TATA boxes can be linked to a DNA fragment encoding a promoter, which functions in plants. Plant promoters can be found commercially or can be synthesized chemically by referring to their published sequence. As example of such a fragment, there may be mentioned the truncated 35S promoter of the cauliflower mosaic virus, which retains its CAAT and TATA boxes. It is possible to use other promoters such as those for nopaline synthase and ribulose 1,5-bisphosphate carboxylase. The promoter fragment is then linked to the heterologous coding sequence. The 3' end of the coding sequence is fused with a polyadenylation site, for example and with no limitation being implied, that of nopaline synthase. In addition, it is possible to use plant transformation vectors which contain one or more polyadenylation sites surrounded with sequences required for the transformation of plants.

The elements of the URE of maize α-tubulin and the heterologous coding sequences of the invention may be subcloned into a polylinker site of a plant transformation vector so as to obtain the chimeric genes.

The 5' elements of the present invention can be derived from the digestion of a maize α-tubulin genomic clone with a restriction and endonuclease or an exonuclease. The restriction fragments containing the CAAT and TATA boxes are ligated to a heterologous gene without promoter such as a coding sequence of GUS or of aroA. A person skilled in the art knows that the 5' regulatory elements of maize α-tubulin can be obtained by other means, for example by chemical or enzymatic (PCR) synthesis. The heterologous product may be the coding sequence of any gene, which may be expressed in such a construct. All these examples form part of the invention. The 3' end of the coding sequence is optionally fused with a polyadenylation site, such as and with no limitation being employed, that of nopaline synthase, that of gene 7 of octopine T-DNA or that of gene H4A748 of the Arabidopsis histone gene. Moreover, the polyadenylation site may be provided by the heterologous gene itself.

The 5' regulatory elements of maize α-tubulin which do not contain a TATA box can be linked to at least part of the plant promoter sequence, that is to say containing at least the CAAT and TATA sequence. Preferably, this promoter is the truncated 35S promoter of the cauliflower mosaic virus. The resulting chimeric complex can be ligated to a heterologous coding sequence and a polyadenylation sequence.

In order to obtain a regulated expression of the heterologous genes, the plants are transformed with the chimeric genes according to the invention. The gene transfer is well known in the art as a method for expressing heterologous genes in transgenic plants. Tobacco is the plant most often used because it is easy to regenerate, the high yield of seeds per plant and because it can be transformed with a high frequency with vectors derived from Agrobacterium Ti plasmids (Klee et al. (1987) *Annu. Rev. Plant Physiol.* 38, 467). Dicotyledonous plants such as, with no limitation being implied, cotton, rape plant and soya bean are the preferred transgenic hosts. However, it will be within the capability of a person skilled in the art that any plant can be efficiently transformed and regenerated as transgenic host according to the invention.

Numerous transformation methods are known. The chimeric genes can be introduced by a process of transformation on foliar disc and regeneration as described by (Horsch et al. (1985) *Science* 227, 1229). Other transformation methods, such as protoplast culture (Horsch et al. (1984) *Science* 223, 496; DeBlock et al. (1984) *EMBRO J* 2, 2143; Barton et al. (1983) *Cell* 32, 1033) or in vitro transformation of explants of stems or roots (Zambrisky et al. (1983) *EMBO J* 2, 2143; Barton et al. (1983) *Cell* 32, 1033) can also be used within the framework of the invention. Preferably, the plants are transformed with vectors derived from Agrobacterium. However, other methods are available for inserting the chimeric genes of the invention into the plant cells. Among these methods, there may be mentioned the approaches by biolistic (Klein et al. (1983) *Nature* 327 70), electroporation, absorption of DNA by chemical induction and the use of viruses or pollens as vectors.

If necessary for the transformation method, the chimeric genes according to the invention can be introduced into a plant transformation vector, for example the binary vector described by Bevan (1984) or another method described in European Application 337 899. The plant transformation vectors may be derived by modification of the natural *Agrobacterium tumefaciens* gene transfer system. The natural system comprises large Ti (Tumour inducing) plasmids containing a large segment, called T-DNA, which is transferred to the transformed plants. Another segment of the Ti plasmid, the vir region is responsible for the transfer of the T-DNA. The T-DNA is surrounded by terminal repeats. In the modified binary vectors, the genes which induce the tumour have been deleted and the functions of the vir region are used to transfer the foreign DNA bordered by the T-DNA border sequences. The T region also contains a selectable marker for resistance to an antibiotic, and a multiple cloning site for the insertion of the sequences to be transferred. These genetic engineering strains are known as "disarmed" *Agrobacterium tumefaciens* and they allow an efficient transformation of the sequences bordered by the T region in the plant nuclear genome.

The surface-sterilized foliar discs are innoculated with *Agrobacterium tumefaciens* containing the foreign DNA, cultured for two days and then transferred into a medium containing antibiotics. The transformed shoots are chosen after rooting in a medium containing the appropriate antiobiotic and transferred into soil. The transgenic plants are self-pollinated and the seeds of these plants harvested and cultivated in a medium containing the antibiotic.

The expression of a reporter or heterologous gene in the roots, the shoots, the pollen, the meristems and the immature embryos can be monitored by immunological or histochemical tests or tests of activity.

As will be seen below, the choice of a test for the expression of the chimeric gene depends on the nature of the heterologous coding region. For example, Northern analysis can be used to monitor the transcription if appropriate nucleotide probes are available. If an antibody is available for the polypeptide encoded by the heterologous gene, Western analysis and immuno-histochemical localization to monitor the production and the localization of the polypeptide can be used. Depending on the heterologous gene, biochemical tests can be used. For example, acetyltransferases are detected by measuring the acetylation of a standard substrate. The expression of a herbicide resistant gene can be monitored by determining the herbicide resistance of the transformed plant.

The invention also comprises both monocotyledonous and dicotyledonous transgenic plants and their progeny containing the chimeric genes according to the invention. Plant cells are transformed with the chimeric genes by any method for transforming plants described above. The transformed plant cell, usually in a callus or foliar disc culture, is regenerated into a complete transgenic plant by methods well known to a person skilled in the art (e.g. Horsch et al. (1985) *Science* 227, 1129). Preferably, the transgenic plant is cotton, rape plant, maize, tobacco or soya bean. As the progeny of the transformed plants transmits the chimeric gene, the seeds or the explants derived from the transformed plants are used to maintain the transgenic plant line.

The invention also comprises a method for producing a plant with an improved herbicide resistance. This method comprises the transformation of a plant cell with a vector containing a chimeric gene comprising a regulatory element, specific for the roots or the meristems, linked to the coding sequence of a herbicide resistance enzyme or a herbicide-degrading enzyme and selection of a plant with the desired properties. Preferably, the elements are regions of the URE of α-Tub 1 comprising nucleotides 1 to 1115, 963 to 1115 or 1 to 1529 as indicated in SEQ ID No.: 1. The transformed plants are regenerated into plants which are resistant to a herbicide application.

The invention also comprises a method for producing a sterile male plant. This method comprises the transformation of a plant cell with a vector containing a chimeric gene comprising a regulatory element, specific for the pollen, linked to the coding sequence of a cytotoxic protein and selection of a plant with the desired properties. Preferably, the elements are the regions of the URE of α-Tub 1 comprising the nucleotides 1 to 1348 or 1295 to 1348 as indicated in SEQ ID No.: 1. The transformed plants are regenerated into plants which are sterile males.

The invention also comprises a method for producing a plant resistant to a herbicide. This method comprises the transformation of a plant cell with a vector containing a chimeric gene comprising a regulatory element, specific for the roots, linked to the coding sequence of a gene for resistance to a herbicide such as N-phosphonomethylglycine, the plants with the desired herbicide resistance then being selected. The selected plants are those which survive a herbicide treatment which kills the non-transformed plants of the same species under the same conditions. Preferably, the elements are regions of the URE of α-Tub 1 comprising nucleotides 1 to 1115, 963 to 1115 or 1 to 1529 as indicated in SEQ ID No.: 1 and the heterologous sequence is provided by a gene encoding EPSPS synthase, acetolactase synthase or 4-hydroxyphenylpyruvate dioxygenase or having mutations making them resistant. The transformed plants are regenerated into plants which are resistant to a herbicide. Preferably, the plants are transformed with a vector pRPA-RD-65 or pRPA-RD-88) which contains the regulatory element specific for the roots comprising nucleotides 70 to 1529 of the URE of α-Tub 1, a monocot intron (pRPA-RD-88 alone), an optimized transit peptide and a herbicide resistance gene aroA.

The following examples illustrate the invention more fully.

The nucleotide sequences to which reference is made in the examples are numbered SEQ ID No.: 1 to 4.

DESCRIPTION OF THE PREFERRED EMBODIMENTS

Example 1 a) Construct with the GUS Reporter Gene

Figure 1:
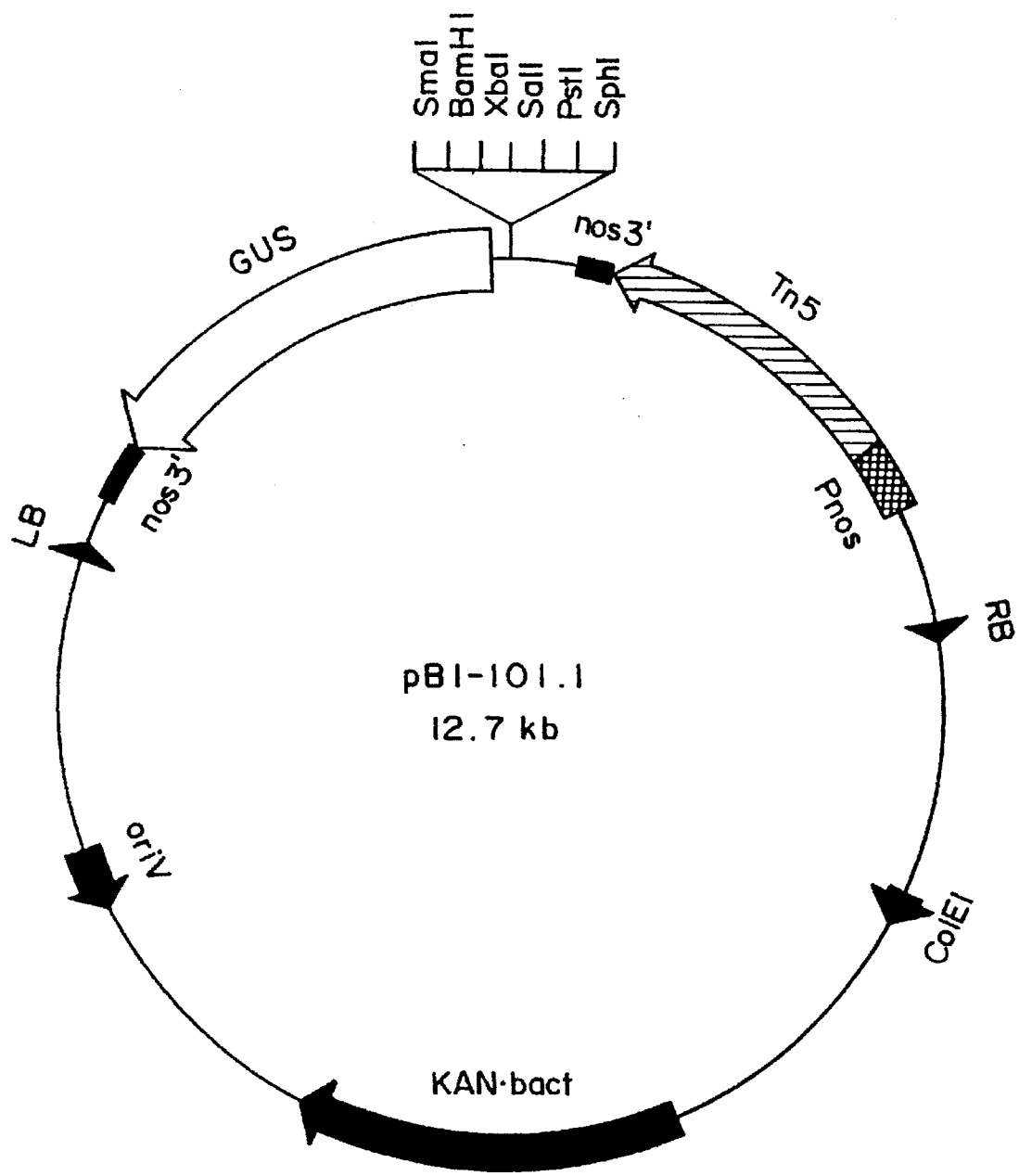
FIG. 1 represents the construction of the parental plasmid p.BI101.1.

The cassettes for general use of the GUS reporter gene which are used in the examples were described by Jefferson et al., 1987 *EMBO J* 6, 3901. In short, the coding sequence of GUS was ligated to the 5' part of the polyadenylation site of nopaline synthase in the polylinker site of the vector pBIN19 derived from *A. tumefaciens* (Bevan (1984) *Nucleics Acids Res.* 12, 8711). The vector pBIN19 contains the left and right borders of T-DNA necessary for the plant transformation, and a kanamycin resistance gene. The resulting construct, pBI101.1 is described in FIG. 1. Only the restriction sites upstream of the initiation codon AUG for GUS allow the insertion of the promoter DNA fragments.

Table 1 describes the parental plasmids and the derived constructs. The maize α-Tub 1 and the positions of the promoter elements contained in the derived constructs are represented in FIG. 2.

Figure 2:
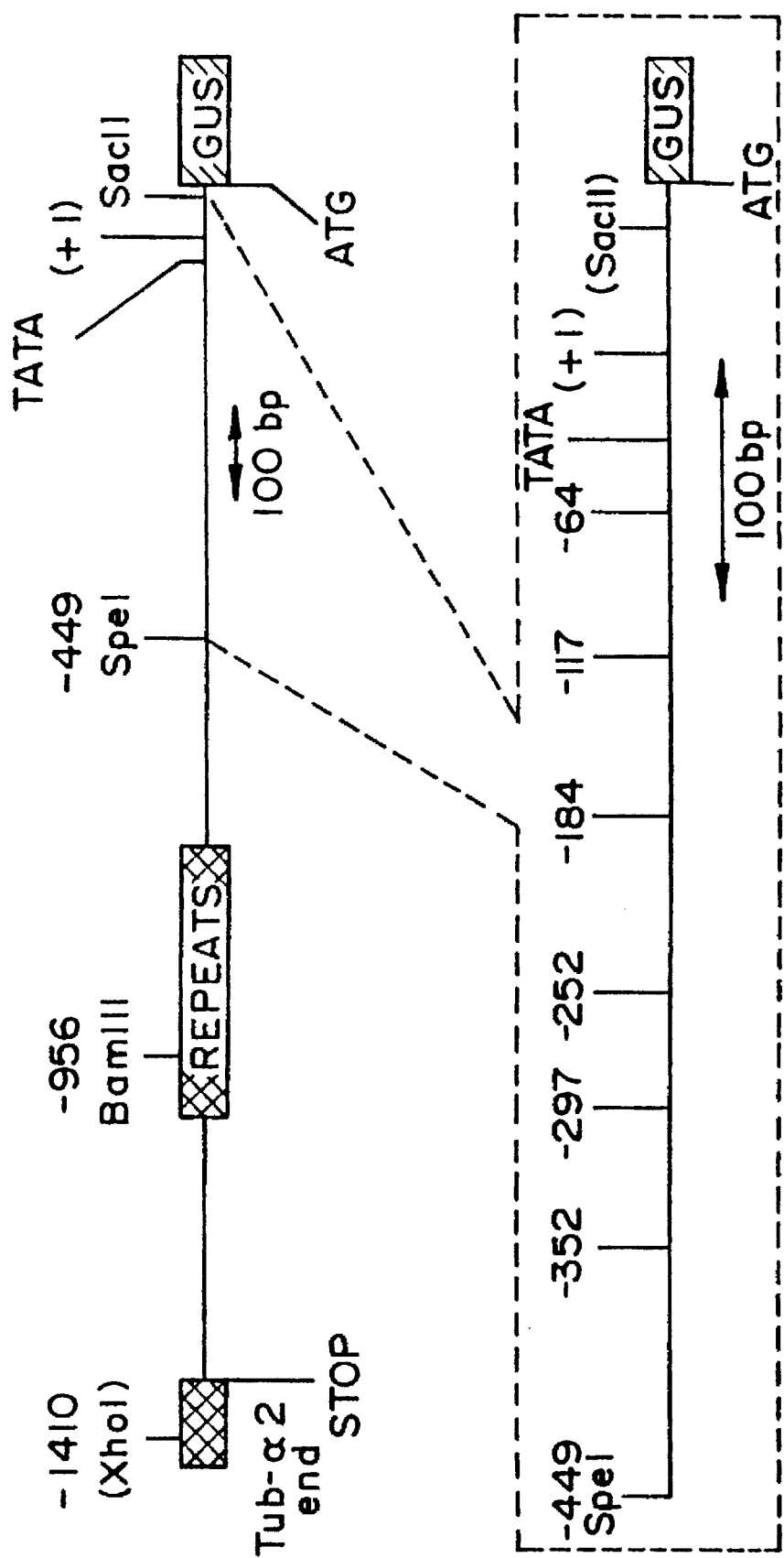
FIG. 2 is a schematic representation of the chimeric constructs α-Tub 1/GUS promoter. The numbers are given relative to the site of initiation of transcription. The top figure corresponds to the intergenic region between α-Tub 1 and α-Tub 2 and the deletions were made by restricting at the appropriate sites. The bottom figure corresponds to fragment −449 where the deletions were made by digesting several times with exonuclease III. The SacII site (+48) corresponds to the transcriptional fusion point between the promoter and the plasmid pBI101.1. (+) corresponds to the site of initiation of transcription of the tubulin gene α-Tub 1.

The constructs pα-Tub 1-GUS represent large overlapping fragments which span the entire length of the regulatory region (−1410 to 48 of FIG. 2). The 5' ends of several constructs were derived from exonuclease III digestions of a 497 bp of α-Tub 1 in pBI101.1 (Stratagene) [−449(SpcI-SacII), Table 1]. The position of each deletion is shown in FIG. 2.

b) Transformation of the Plants

The plasmid constructs based on pBIN19 were used to transform tobacco (*Nicotinia tabacum* cv petite Havana SR1) according to standard procedures (Horsch et al. (1985) except that the initial transformants were selected on 100 μg/ml of kanamycin.

The plants were self-pollinated, and the F1 sheaths allowed to germinate on 200 g/ml of kanamycin in order to identify the transformants, since the constructs based on pBIN19 contain the neomycin phosphotransferase (NPTII) gene which confer the resistance to the toxic kanamycin antibiotic. The copy number of each GUS construct integrated into the tobacco genome was estimated for each transformant by analyzing the segregation frequencies for the resistance to the kanamycin. Most of the transformants contained only a locus segregating from the construct. The transgenic plants were grown in a greenhouse.

TABLE I

| Construct | Description |
|---|---|
| Parental plasmids | |
| pBI101.1 | pBIN-19 cassette of the gene, without promoter, derived from the GUS reporter gene (Jefferson et. al., 1987) (cf. FIG. 1). |
| pRPA-BL-504 | similar to pBI101.1 except that the gene for chloramphenicol acetyltransferase replaces the GUS gene. |
| pαTub 1 | XhoI fragment of 3058 bp from MG19/6 (Montoliu et. al., 1989) cloned into pUC-18; contains the entire upstream regulatory ensemble of maize α-Tub 1. |
| pαTub 1-1588 | XhoI-AluI fragment of 1588 bp from maize α-Tub 1 (Montoliu et. al., 1989) cloned into pUC-18; contains 1410 bp upstream and 180 bp downstream of the site for initiation of transcription. |

TABLE I-continued

| Construct | Description |
|---|---|
| pαTub 3-1072 | BglII fragment of 1072 bp from maize αTub 3 (Montoliu et. al., 1990) cloned into the BamHI site of pUC-18; contains 1020 bp upstream and 62 bp downstream of the site of initiation of transcription. |
| pRPA-RD-37B | aroA expression cassette containing an optimized transit peptide fused in frame (EP 508 909), an aroA gene and an NOS polyadenylation signal cloned into pBS II SK(-) (Stratagene). |
| pRPA-RD-49 | monocot transformation vector containing a 35S CaMV promoter, a bar gene and a TR7 polyadenylation signal cloned between the HindIII and EcoRI sites of pUC-18. An NotI linker was ligated to the blunt end between the two AflIII sites and SspI site and creating a 3.1 kb NotI fragment containing the gene construct 35S CaMV - bar. |
| pRPA-RD-26 | EcoRI-ScaI fragment of 1865 bp from pαTub 1 cloned into EcoRI-HincII digested pUC-19. The sequence surrounding the ATG for initiation of translation was mutated by PCR so as to contain an NcoI site using the 5'->3' C GGC CGC CGC TCC ACC CGT ACG ACG ACC ACC ATG GGG GAG. |
| pRPA-RD-32 | a PstI-NcoI fragment of 1458 bp from pRPA-RD-26 consisting of nucleotides -1340 to 118 derived from the maize gene α-Tub 1 (nucleotides 71 to 1527 of SEQ ID NO. 1) was ligated into the PstI-NcoI sites of pRPA-RD-37B creating an expression cassette maize α-Tub 1-OTP-aroA gene-NOS. |
| pRPA-RD-87 | an NcoI-PstI fragment of 600 bp containing maize adhI intron 1 was cloned into the NcoI-PstI sites of pRPA-RD-37B creating an expression cassette: maize adhI intron 1 - optimized transit peptide (EP 508 909), aroA gene and NOS polyadenylation signal. |
| pRPA-RD-90 | an EagI fragment of 1430 bp derived from pRPA-RD-32 (containing nucleotides -1340 to 90 of the maize gene α-Tub 1; sequence 71 to 1499 of SEQ ID NO. 1) cut with a blunt end by the Klenow fragment of DNA polymerase I of E. coli DNA cloned into the SmaI site of pBS II SK(-) (Stratagene). |

Derived constructs

| | |
|---|---|
| -1410 | HindIII-SacII fragment of 1474 bp from pαTub 1-1588 cloned into HindIII-SmaI digested pBI101.1; contains 1410 bp upstream and 48 bp downstream of the site of initiation of transcription. |
| α-Tub 3-1020 | HindIII-SmaI fragment of 1115 bp from pαTub 3-1072 cloned into HindIII-SmaI digested pBI101.1; contains 1020 bp upstream and 62 bp downstream of the site of initiation of transcription (cf FIG. 2). |
| -956 | a -1410 derivative generated by BamHI digestion and recircularization; contains 956 bp upstream and 48 bp downstream of the site of initiation of transcription. |
| -449 | a -1410 derivative generated by SpeI digestion and recircularization; contains 449 bp upstream and 48 bp downstream of the site of initiation of transcription. |
| -352 | -449 derivative (in pBI101.1) generated by exonuclease III digestion and recircularization; contains 352 bp upstream and 48 bp downstream of the site of initiation of transcription. |
| -297 | a -449 derivative (in pBI101.1) generated by exonuclease III digestion and recircularization; contains 297 bp upstream and 48 bp downstream of the site of initiation of transcription. |
| -252 | a -449 derivative (on pBI101.1) generated by exonuclease III digestion and recircularization; contains 252 bp upstream and 48 bp downstream of the site of initiation of transcription. |
| -184 | a -449 derivative (in pBI101.1) generated by exonuclease III digestion and recircularization; contains 184 bp upstream and 48 bp downstream of the site of initiation of transcription. |
| -117 | a -449 derivative (in PBI101.1) generated by exonuclease III digestion and recircularization; contains 117 bp upstream and 48 bp downstream of the site of initiation of transcription. |
| -64 | a -449 derivative (in pBI101.1) generated by exonuclease III digestion and recircularization; contains 64 bp upstream and 48 bp downstream of the site of initiation of transcription. |
| pRPA-RD-53 | a SacI-EcoRI fragment of 3.5 kb containing the expression cassette maize α-Tub 1-aroA from pRPA-RD-32 cloned into the SacI-EcoRI sites of pBIN-19. |
| pRPA-RD-65 | a SacI-EcoRI fragment of 3.5 kb containing the expression cassette maize α-Tub 1-aroA from pRPA-RD-32 rendered blunt ended by T4 DNA polymerase cloned into the NdeI site of pRPA-RD-49 which was cut with a blunt end by Klenow fragment of DNA polymerase of E. coli. The orientation of the expression cassette maize α-Tub 1-aroA from pRPA-RD-32 proved to be divergent in relation to the transcription units of the aroA and bar gene. |
| pRPA-RD-88 | a PstI fragment of 1.5 kb from PRPA-RD-90 containing nucleotides -1340 to 90 of the maize α-Tub 1 gene (sequence 71 to 1499 of SEQ ID No. 1) cloned into the PstI site of PRPA-RD-87 with creation of an expression cassette: maize α-Tub 1 - maize adhI intron 1 - optimized transit peptide (EP 508 909), aroA gene and NOS polyadenylation signal. |
| pRPA-RD-7: | a derivative of the optimized transit peptide (EP 508 909; SEQ ID NO: 4) which was mutated by PCR with the following synthetic oligonucleotides: (1) GAA TTC CGA AAG ACA AAG ATT ATC GCC ATG GCT TCG [nucleotides 1–36; SEQ ID NO: 3]; (2) CCG TAG GCC GGC CAC ACC TGC ATA CAT TGA ACT CTT CC [nucleotides 228–181; SEQ ID NO: 3]; and (3) CGA GAC GCT GTC GTA CCT GCC GCC GCT GTC TAT GGC G [nucleotides 231–267; SEQ ID NO: 3]. This optimized transit peptide was cloned into the EcoRI and EcoRV sites of pBSII SK(-) [Stratagene] with creation of a cloning cassette containing the optimized transit peptide. |

Example 2

Histochemical Localization of the GUS Activity; Expressions Specific for the Roots and the Pollen The GUS activity was determined in the roots, the pollen and various other tissues of transgenic tobacco each containing constructs and is represented in Table 1. The conventional procedures of Jefferson et al. (1987) were followed.

The GUS activity was histochemically localized in transgenic plants containing chimeric GUS genes using promoter fragments derived from the maize α-Tub 1 gene. Samples were washed in a mixture of 50 mM NaPO$_4$, pH 7, 0.2 mM 5-bromo-4-chloro-3-indolyl-glucuronide (X-Gluc), 0.1 mM potassium ferricyanide and 0.1 mM potassium ferrocyanide. The samples were mounted on microscope slides covered with 80% glycerol.

Table 2 represents, in summarized form, the results of typical microphotographs of tobacco plants containing regulatory elements of the maize α-Tub 1 gene. Table 2 shows that the regulatory elements of α-Tub 1 give high expression levels in the meristematic tissues, in particular the meristems of roots and the pollen.

The GUS activity was analyzed by fluorometry by grinding the plant tissue in an extraction buffer (50 mM NaPO$_4$, 10 mM EDTA, 0.1% Sarkosyl, 0.1% Triton X-100 and 10 mM of β-mercaptoethanol). After centrifugation of the lysate, the supernatant is removed and placed in a new tube and added in aliquots of 100 μl. An equal volume of 2 mM of 4-methylumbelliferyl-γ-glucuronide in the extraction buffer was added and incubated at 37° C. for 1 hour. The reactions were stopped with 0.8 ml Na$_2$ CO$_3$ (0.2M). The fluorescence of 4-methylumbelliferone (4-MU) was determined with a Hoeffer minifluorometer as described by Jefferson et al. (1987). The GUS activity is expressed in picomoles of 4-MU per unit of total mass of protein per minute. To determine the promoter elements responsible for the meristem specificity with respect to the expression specific for the pollen, the pattern of expression of GUS of various deletions of promoters (cf FIG. 2) was determined in the transgenic tobacco plants.

Root tips, shoot tips, leaves, stems and pollen derived from transgenic plants containing various sequence elements of α-Tub 1 (summarized in FIG. 2) directing the expression of GUS were tested with respect to the activity. The results are presented in Table 3. All the constructs containing a portion of the URE of the α-Tub gene of maize α-tubulin between −1410 and −352 (SEQ ID No. 1: 1 to 1058) conferred a GUS activity in the roots of transgenic tobaccos. The total length of the regulatory region and the fragments derived therefrom all confer a high activity in tobacco protoplasts. It is only after deletion of promoter elements closer than 352 bp upstream of the site of initiation of transcription (1058 of SEQ ID No. 1) that the GUS activity is suppressed in the transgenic roots, which shows that the regulatory elements specific for the roots of α-Tub 1 are upstream of −352 bp (SEQ ID No. 1: 1 to 1058).

All the constructs containing a portion of the URE of the α-Tub gene of maize α-tubulin between −1410 and −64 (SEQ ID No. 1: 1 to 1058) conferred a GUS activity in the pollen of transgenic tobaccos. It is only after deletion of promoter elements closer than 64 bp upstream of the site of the initiation of transcription (1348 of SEQ ID No. 1) that the GUS activity is suppressed in the transgenic pollen, which shows that the regulatory elements specific for the pollen of α-Tub 1 are upstream of −64 bp (SEQ ID No. 1: 1 to 1058).

TABLE 2

Histochemical analysis of transgenic plants

| Construct | TISSUE | | | | |
|---|---|---|---|---|---|
| | root tip | shoot tip | leaf | stem | pollen |
| −1410 | +(12/12) | −(12/12) | −(12/12) | −(12/12) | +(12/12) |
| −956 | +(6/6) | −(6/6) | −(6/6) | −(6/6) | +(6/6) |
| −449 | +(8/8) | −(8/8) | −(8/8) | −(8/8) | +(8/8) |
| −352 | −(12/13) | −(13/13) | −(13/13) | −(13/13) | +(6/10) |
| −117 | −(9/9) | −(9/9) | −(9/9) | −(9/9) | +(4/9) |
| −64 | −(11/11) | −(11/11) | −(11/11) | −(11/11) | −(11/11) |

The figures indicate the number of plants with a blue spot (+) or without (−) the expression compared with the entire plants analyzed, for each construct in various parts of the plant.

TABLE 3

Fluorometric test if the GUS constructs with a promoter of the α-Tub 1 gene of maize α-tubulin from transgenic tobacco plants

| Construct | days after germination | TISSUE | | | | | |
|---|---|---|---|---|---|---|---|
| | | whole root 2 | control plant root 2 | whole leaves | control plant leaf 2 | cotyledon 2 | control plant cotyledon 2 |
| −1410 | 10 | 388 ± 124 | 15 | 39 ± 2 | 13 | | |
| | 15 | 727 ± 736 | 16 | 61 ± 55 | 14 | | |
| | 25 | 265 ± 233 | 20 | 15 ± 2 | 15 | 148 ± 56 | 15 |
| −956 | 10 | 3082 ± 1551 | 15 | 736 ± 499 | 13 | | |
| | 15 | 4934 ± 557 | 16 | 612 ± 363 | 14 | | |
| | 25 | 237 ± 170 | 20 | 30 ± 15 | 15 | 86 ± 52 | 15 |
| −449 | 10 | 405 ± 40 | 15 | 73 ± 64 | 13 | | |
| | 15 | 70 ± 28 | 16 | 118 ± 134 | 14 | | |
| | 25 | 469 | 20 | 19 ± 8 | 15 | 172 ± 57 | 15 |
| −352 | 10 | 466 | 15 | 127 | 13 | | |
| | 15 | 15 | 16 | 13 ± 2 | 14 | | |
| | 25 | 26 ± 10 | 20 | 27 ± 2 | 15 | 5 ± 2 | 15 |

Example 3

Histochemical Localization of GUS Activity: Expression Specific for the Meristems The GUS activity was localized histochemically in transgenic plants containing chimeric GUS genes using promoter fragments derived from the maize α-Tub 3 gene (nucleotides 1 to 1082 SEQ ID No. 3). Samples were washed in a mixture of 50 mM NaPO$_4$, pH 7; 0.2 mM 5-bromo-4-chloro-3-indolyl-glucuronide (X-Gluc); 0.1 mM potassium ferricyanide and 0.1 mM potassium ferrocyanide. The samples were mounted on microscope slides covered with 80% glycerol.

Table 4 presents, in summarized form, the results of typical microphotographs of tobacco plants containing regulatory elements of the maize α-Tub 3 gene. Table 4 shows that the regulatory elements of α-Tub 3 (nucleotides 1 to 1082 SEQ ID No. 3) give high levels of expression preferably in the meristematic tissues.

Figure 3:
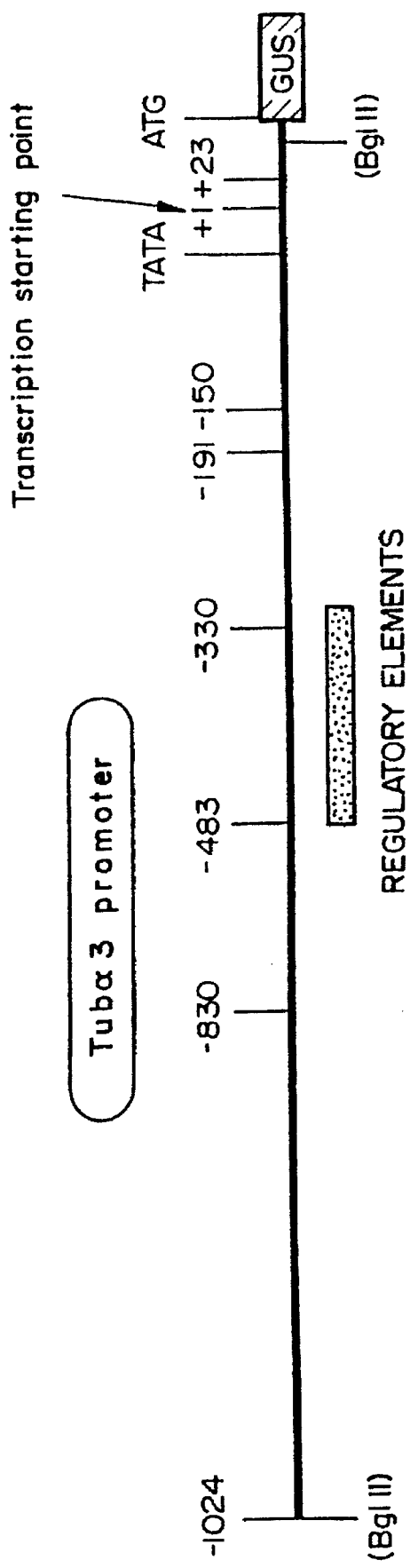
FIG. 3 is a schematic representation of the chimeric constructs α-Tub 3/GUS promoter. The numbers are given relative to the site of initiation of transcription. The deletions were made by digesting several times with exonuclease III. The BglII site corresponds to the transcriptional fusion point between the promoter and the BamHI site of the plasmid pBI101.1. (+) corresponds to the site of the initiation of transcription of the tubulin gene α-Tub 3.

The GUS activity was analyzed by fluorometry by grinding the plant tissue in an extraction buffer (50 mM NaPO$_4$, 10 mM EDTA, 0.1% Sarkosyl, 0.1% Triton X-100 and 10 mM of β-mercaptoethanol). After centrifugation of the lysate, the supernatant is removed and placed in a new tube and 100 μl aliquots added. An equal volume of 2 mM 4-methylumbelliferyl-β-glucuronide in the extraction buffer is added and incubated at 37° C. for 1 hour. The reactions are stopped with 0.8 ml Na$_2$CO$_3$ (0.2M). The fluorescence of 4-methylumbelliferone (4-MU) was determined with a Hoeffer minifluorometer described by Jefferson et al. (1987). The GUS activity is expressed in picomols 4-MU per unit of total mass of protein per minute. To determine the promoter elements responsible for the meristematic specificity with respect to the expression specific for the meristems, the pattern of expression of GUS of various deletions of promoters (cf. FIG. 3) was determined in the transgenic tobacco plants.

TABLE 4

Fluorometric test of the GUS constructs with a promoter of the α-Tub 3 gene of maize α-tubulin from transgenic tobacco plants

| days after germination | TISSUE | | | |
|---|---|---|---|---|
| | root apex | control plant root apex | shoot apex | control plant shoot apex |
| 12 | 12.88 ± 6.68 | 3.65 | 39.02 ± 22.04 | 2.85 |
| 16 | 7.31 ± 3.63 | 3.56 | 33.22 ± 22.00 | 1.93 |

TABLE 4-continued

Fluorometric test of the GUS constructs with a promoter of the α-Tub 3 gene of maize α-tubulin from transgenic tobacco plants

| days after germination | TISSUE | | | |
|---|---|---|---|---|
| | root apex | control plant root apex | shoot apex | control plant shoot apex |
| 19 | 47.67 ± 35.90 | 4.78 | 20.53 ± 4.00 | 3.06 |
| 23 | 27.17 ± 20.93 | 5.97 | 28.35 ± 10.97 | 0.42 |
| 26 | 31.77 ± 13.81 | 4.82 | 35.66 ± 30.88 | 1.85 |
| 30 | 20.64 ± 12.44 | 8.10 | 29.40 ± 17.88 | 3.81 |

The plants were stably transformed with a promoter fragment −1024 fused to the GUS reporter gene. The results are expressed in pmol/h×mg of protein and correspond to the mean of 6 to 15 plants of the progeny of each of the 4 independent transformed F1 plants.

Example 4

Introduction of Herbicide Resistance into Tobacco

The SacI-EcoRI fragment of 3.5 kb derived from the parental plasmid pRPA-RD-32 (cf Table 1) was cloned into the SacI-EcoRI sites of pBIN-19. The resulting construct, called pRPA-RD 53, comprises in the transcription frame, the following elements: the maize α-Tub 1 regulatory element, the optimized transit peptide (OTP), the aroA gene, the nos terminator.

The parental plasmid pRPA-RD-53 was transferred into the strain EHA 105 *Agrobacterium tumefaciens* (Hood et al. (1986) *J. Bacteriol*, 168, 1291) by triparental crossing and the resulting Agrobacterium was used for the transformation on tobacco foliar disc.

The regenerated tobacco plants, about 20 cm high, were sprayed in a greenhouse with glyphosate formulated in the form of Round Up. The transformed plants containing pRPA-RD-53, which were viable and in good health, showed increased tolerance to glyphosate.

We claim:

1. An expression construct for conferring root specific expression in plants which comprises a regulatory sequence of maize α-tubulin consisting of nucleotides 1 to 1115 of SEQ ID NO:1.

2. An expression construct for conferring root specific expression in plants which comprises a regulatory sequence of maize α-tubulin consisting of nucleotides 963 to 1115 of SEQ ID NO:1.

3. An expression construct for conferring root specific expression in plants which comprises a regulatory sequence of maize α-tubulin consisting of nucleotides 1 to 1529 of SEQ ID NO:1.

4. An expression construct for conferring pollen specific expression in plants which comprises a regulatory sequence of maize α-tubulin consisting of nucleotides 1 to 1348 of SEQ ID NO:1.

5. An expression construct for conferring pollen specific expression in plants which comprises a regulatory sequence of maize α-tubulin consisting of nucleotides 295 to 1348 of SEQ ID NO:1.

6. An expression construct for conferring meristem specific expression in plants which comprises a regulatory sequence of maize α-tubulin consisting of nucleotides 1 to 695 of SEQ ID NO:3.

7. An expression construct for conferring meristem specific expression in plants which comprises a regulatory sequence of maize α-tubulin consisting of nucleotides 542 to 695 of SEQ ID NO:3.

8. An expression construct for conferring immature embryo specific expression which comprises a regulatory sequence of maize α-tubulin consisting of nucleotides 1 to 1076 of SEQ ID NO:3.

9. An expression construct further comprising in the 5' to 3' direction the regulatory sequence of any of claims 1, 2 and 4–8 operably linked to a promoter which functions in plants.

10. The expression construct of claim 9 wherein the promoter sequence is one of the 35S promoter from cauliflower mosaic virus, a plant histone promoter, or a rice actin promoter.

11. The expression construct of claim 9 further comprising in the 5' to 3' direction a coding sequence for a heterologous gene operably linked to the promoter.

12. The expression construct of claim 3 operably linked to a coding sequence for a heterologous gene.

13. The expression construct of claim 11 further comprising a polyadenylation site.

14. The expression construct of claim 12 further comprising a polyadenylation site.

15. The expression construct of claim 11 wherein the polyadenylation site is derived from at least one of nopaline synthase gene, gene 7 of octopine T-DNA, or Arabidopsis H4A748 histone gene.

16. The expression construct of claim 12 wherein the polyadenylation site is derived from at least one of nopaline synthase gene, gene 7 of octopine T-DNA, or Arabidopsis H4A748 histone gene.

17. The expression construct of claim 9 further comprising an intron sequence operably linking the promoter and coding sequence for a heterologous gene.

18. The expression construct of claim 3 further comprising an intron operably linking the regulatory sequence to a coding sequence for a heterologous gene.

19. The expression construct of claim 11 wherein the coding sequence for a heterologous gene is derived from at least one of an enzyme for the metabolism of lipids, a desaturase, or a herbicide resistance gene.

20. The expression construct of claim 12 wherein the coding sequence for a heterologous gene is derived from at least one of a gene encoding 5-enolpyruvylshikimate-3-phosphate synthase, acetolactase or 4-hydroxyphenylpyruvate dioxygenase (HPPO).

21. The expression construct of claim 11 wherein the heterologous gene is the aroA gene for resistance to glyphosate.

22. The expression construct of claim 12 wherein the heterologous gene is the aroA gene for resistance to glyphosate.

23. A plant cell comprising the expression construct of at least one of claims 1–8.

24. A plant cell comprising the expression construct of claim 9.

25. A plant cell comprising the expression construct of claim 10.

26. A plant cell comprising the expression construct of claim 11.

27. A plant cell comprising the expression construct of claim 12.

28. A plant or plant progeny, regenerated from a plant cell according to claim 23.

29. The plant or plant progeny of claim 28, wherein the plant is a monocotyledon.

30. The plant or plant progeny of claim 28, wherein the plant is maize or a cereal.

31. The plant or plant progeny of claim 28, wherein the plant is a dicotyledon.

32. The plant or plant progeny of claim 28, wherein the plant is tobacco, cotton or soybean.

33. A process for producing a plant with an improved agronomic property, which comprises:

a) transforming a plant cell with the expression construct of claim 11; and b) regenerating the plant.

34. The expression construct of claim 12 wherein the coding sequence for a heterologous gene is derived from at least one of an enzyme for the metabolism of lipids, a desaturase or a herbicide resistance gene.

35. The expression construct of claim 11 wherein the coding sequence for a heterologous gene is derived from at least one of a gene encoding 5-enolpyruvylshikimate-3-phosphate synthase, acetolactase or 4-hydroxyphenylpyruvate dioxygenase (HPPO).

* * * * *

UNITED STATES PATENT AND TRADEMARK OFFICE
CERTIFICATE OF CORRECTION

PATENT NO. : 5,635,618
DATED : June 3, 1997
INVENTOR(S) : M. Capellades, et al.

It is certified that error appears in the above-identified patent and that said Letters Patent are hereby corrected as shown below:

Column 3, line 39: "mariner" should read --manner--

Column 6, line 30: "115" should read --1115--

Column 12, line 43: "PRPA-RD-87" should read --pRPA-RD-87--

Signed and Sealed this

Fourteenth Day of March, 2000

Attest:

Attesting Officer

Q. TODD DICKINSON

Commissioner of Patents and Trademarks